United States Patent
Keller

(10) Patent No.: US 6,187,006 B1
(45) Date of Patent: Feb. 13, 2001

(54) SURGICAL INSTRUMENT

(75) Inventor: Arnold Keller, Kayhude (DE)

(73) Assignee: Waldemar Link (GmbH & Co.), Hamburg (DE)

( * ) Notice: Under 35 U.S.C. 154(b), the term of this patent shall be extended for 0 days.

(21) Appl. No.: 09/300,493

(22) Filed: Apr. 28, 1999

(30) Foreign Application Priority Data

Apr. 28, 1998 (DE) ......................................... 298 07 670 U

(51) Int. Cl.[7] ............................................... A61B 17/56
(52) U.S. Cl. .............................................. 606/67; 623/22
(58) Field of Search ............................... 606/67, 85, 95, 606/99, 79, 86; 623/11, 22, 23

(56) References Cited

U.S. PATENT DOCUMENTS

| | | |
|---|---|---|
| 4,990,149 | 2/1991 | Fallin . |
| 5,089,003 | * 2/1992 | Fallin et al. .................... 606/85 |
| 5,443,471 | 8/1995 | Swajger . |
| 5,951,606 | * 9/1999 | Burke ........................... 623/23 |

FOREIGN PATENT DOCUMENTS

| | | |
|---|---|---|
| 94 07 621 U | 4/1995 | (DE) . |
| 196 31 984 | 2/1998 | (DE) . |
| 0 166 085 | 10/1987 | (EP) . |
| 0 380 309 | 1/1990 | (EP) . |

\* cited by examiner

*Primary Examiner*—Michael Buiz
*Assistant Examiner*—Lien Ngo
(74) *Attorney, Agent, or Firm*—Morrison & Foerster LLP

(57) ABSTRACT

A surgical instrument includes a stem to be inserted into the medullary cavity of a proximal femur and a grip part slightly offset from and extending approximately parallel to the direction of the stem. The grip part is releasably connected to the upper end of the stem by mutual coupling parts including a peg protruding obliquely from the upper end of the stem and a bore located in the lower end of the grip part. Releasable means for arresting the peg in the bore are formed by the end of a rod which is guided movably in the longitudinal direction of the grip part and by a recess in the peg for receiving this end. The recess in the peg is a continuous bore and the rod, in its arrested position, extends completely through the bore. The upper end of the rod is connected to a handle located in the middle to upper region of the grip part. The rod or the handle is provided with a catch mechanism for securing the rod in the arrested position.

19 Claims, 1 Drawing Sheet

SURGICAL INSTRUMENT

FIELD OF THE INVENTION

The present invention relates to surgical instruments used by orthopedic surgeons to prepare a femur for implantation of a prosthesis, and more particularly to a surgical rasp tool which is securely locked during contouring operations, readily manipulated by the surgeon and easy to clean.

BACKGROUND OF THE INVENTION

Before the stem of a hip prosthesis can be inserted into the medullary cavity of the proximal femur, the medullary cavity has to be opened, after resection of the head/neck, and then reamed out and shaped to accommodate the stem that is to be inserted. This is done using a rasp, the stem of which is identical to the configuration of the prosthesis stem. The upper end of the rasp corresponds to the resection plane. Extending from the top of this upper end there is a peg whose direction follows that of the head/neck. This configuration permits a rasp instrument to be applied for the purpose of finishing the resection surface (EP-B-166,085); alternatively, a trial joint head can be placed thereon. The same applies to a trial stem. The rasp can also function as a trial stem.

To insert and release the stem, a grip part is provided which can be connected releasably to the stem via coupling parts. The grip part extends generally parallel to the direction of the stem (DE-U-94 07 621) so that hammer blows on its anvil-shaped end drive the stem home or remove it in substantially the longitudinal direction of the stem.

The coupling parts for connecting the stem to the grip part comprise the peg (described above) located at the upper end of the stem, and a bore located on the grip part which receives this peg. Since the peg extends in the head/neck direction, it protrudes obliquely to the side and away from the stem (in relation to the central longitudinal axis of the stem). To ensure that the lower end of the grip part can receive the stem, the grip part is generally angled off in relation to the direction of the rest of the grip part. Thus, most of the grip part extends with a slight lateral offset in relation to the stem, albeit essentially parallel to the longitudinal axis of the stem.

The coupling parts provided in known instruments of this type also comprise means for arresting the peg in the bore to secure the connection between the stem and the grip part. These arresting means are releasable so that the grip part can be detached from the peg. The known arresting means leave something to be desired. Arresting means designed as a screw connection have the disadvantage that the tightening and releasing of the screw takes some time. Also, such screw connections can come loose under the effect of the blows when the stem is being driven home or withdrawn. In arresting means designed as quick-action connectors, the activation means are typically provided in the immediate vicinity of the coupling arrangements. The disadvantage of such arrangements is that they have to be located and activated deep in the wound. This difficulty also arises in the case of a known instrument (DE-C 196 31 984) in which, in order to couple the stem with the grip part, S-shaped members on these coupling parts have to be brought into engagement before their engagement can be secured by means of a sleeve pushed over them. In yet another coupling arrangement (disclosed in a brochure entitled "Das PCA-H üft-Total-System" from the company Howmedica Kiel), a lever engaging the coupling arrangements can be moved from outside the operating wound. Unfortunately, lever movement is very long, creating a substantial disadvantage given the confined space of the operating field. Finally, most of the known instruments of the type described have the disadvantage that their coupling arrangements are complicated and they are therefore difficult to clean.

Needs exist for surgical rasp tools that address the limitations of the existing instruments.

SUMMARY OF THE INVENTION

In view of the foregoing limitations and shortcomings of the prior art, as well as other disadvantages not specifically mentioned above, there still exists a need in the art for improved rasp tools. It is therefore a primary object of the present invention to fulfill that need by providing an orthopedic instrument that functions reliably, can be readily controlled from outside the immediate wound area, and is easy to clean.

More particularly, the present invention is a surgical instrument that includes a stem to be inserted into the medullary cavity of a proximal femur and a grip part slightly offset from and extending approximately parallel to the direction of the stem. The grip part is releasably connected to the upper end of the stem by mutual coupling parts including a peg protruding obliquely from the upper end of the stem and a bore located in the lower end of the grip part. Releasable means for arresting the peg in the bore are formed by the end of a rod which is guided movably in the longitudinal direction of the grip part and by a recess in the peg for receiving this end. The recess in the peg is a continuous bore, and the rod, in its arrested position, extends completely through the bore. The upper end of the rod is connected to a handle located in the middle to upper region of the grip part. The rod or the handle is provided with a catch mechanism for securing the rod in the arrested position.

One advantageous feature of the present invention is the releasable arresting means. As noted above, the releasable means for arresting the peg in the bore preferably includes a rod which is guided movably in the longitudinal direction of the grip part and whose end engages a corresponding recess of the peg. Known arresting means found in existing instruments include locking arrangements which engage the peg perpendicular to the peg direction. Since this peg direction is at an angle of approximately 45° to the longitudinal direction of the stem and of the grip part, the locking movement direction also extends obliquely, the result of which is that the activation of this lock arrangement must take place directly at the coupling arrangements or must be transmitted via relatively complicated transmission means. A significant difference between the present invention and previously known arresting arrangements lies in the fact that the present invention eliminates perpendicular lock movement. Specifically, in the present invention the lock lies in the longitudinal direction of the grip part, that is to say obliquely in relation to the peg, and is also moved in this direction. The recess provided in the peg for receiving the lock part is also oblique and is expediently designed as a continuous bore. This configuration is relatively straightforward. The parts interact in an uncomplicated manner and can be easily dismantled for cleaning. A particular advantage is that as a result of the parallel relationship between the rod and the grip part, the handle for moving the rod can be arranged at any desired point on the grip part, that is to say, at any desired distance from the operating wound at the end of the grip part remote from the stem, without detracting from the simplicity of construction or increasing space requirements.

The rod is expediently guided in a bore of the coupling part that is open at the bottom, so that it can be easily taken out for cleaning. For example, access to the indented end of the rod is provided through the open bottom of the bore, thereby allowing a screwdriver or other tool to be inserted for unscrewing and releasing the rod from its handle. Above the coupling part, the rod lies in an open groove, further expediting the cleaning operation. Preferably, essentially the entire cross section of the rod is received by the groove, with the groove being open toward one side of the grip part. This configuration allows the user to hold and manipulate the grip part without having to take the location of the rod into consideration.

To ensure that the rod does not inadvertently leave its arrested or stopped position, a catch mechanism is provided. Preferably, the catch mechanism includes a release mechanism connected to the locking means (e.g., rod) for longitudinal displacement with that means. A spring is connected to the release mechanism for urging the release mechanism to a stop, or locked, position. In that locked position, a projection on the release mechanism rests in a small opening or notch located on a handle section of the grip part. To release the locking means, the operator counters the spring force until the projection on the release mechanism exits the small opening or notch. The operator then slides the release mechanism upward, along with the connected locking means, thereby disengaging the means for securing the grip part to the stem. A second notch or opening may be provided for retaining the release mechanism in its "unlocked" position.

The grip part may also include a handle. The handle includes a slide guided for movement in the longitudinal direction of the grip part. The locking means (e.g., rod) is connected to the slide. In those embodiments, the catch mechanism preferably comprises a release mechanism that is pivotally connected to the slide, and a spring for urging the release mechanism toward a flank defining the handle.

To ensure that that part of the rod which interacts with the peg and which may have to transmit considerable forces is held securely, the rod extends completely through the bore in the peg. In other words, the rod is held on both sides of the peg in the guide bore.

These and other objects and features of the invention are apparent in the disclosure, which includes the above and ongoing written specification, with the drawings. The invention is explained in greater detail below with reference to the drawing which shows an advantageous illustrative embodiment.

DETAILED DESCRIPTION OF THE INVENTION

Figure 1:
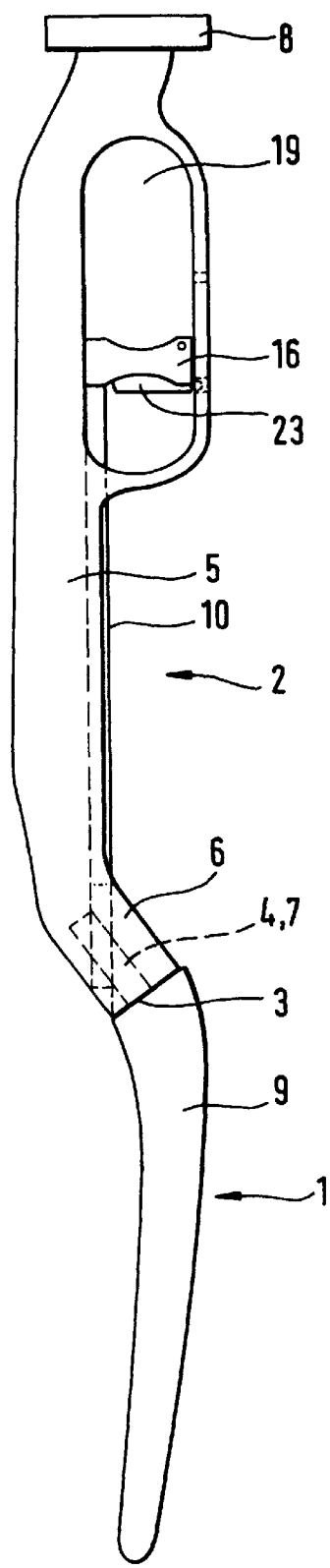
FIG. 1 is a side view of the surgical instrument of the present invention.

As shown in FIG. 1, the rasp 1 is connected to a grip part 2. The rasp 1 comprises a stem 9 which is to be inserted into the medullary cavity of the proximal femur. At the top, it ends in a flat surface 3 which lies obliquely in relation to the longitudinal direction of the stem 9. A peg 4 extends from this surface 3 at a generally perpendicular angle, and thus also obliquely in relation to the longitudinal direction of the stem 9.

The grip part 2 includes an elongate stem 5 which runs approximately parallel to the longitudinal direction (axis) of the rasp stem 9 and is slightly laterally offset with respect to said rasp stem 9. At the bottom, it merges into a coupling part 6 which, corresponding to the oblique direction of the peg 4, runs obliquely with respect to the stem 5 of the grip part and the stem 9 of the rasp 1. The angle between the peg 4 and the coupling part 6, on the one hand, and the longitudinal direction of the rasp stem 9 and of the stem 5 of the grip part 2, on the other hand, corresponds to the CCD angle of the associated prosthesis and is therefore of the same order of magnitude as normal CCD angles. The "CCD angle" as it relates to a femoral prosthesis is the angle that the shaft axis forms with the shank neck axis running through the head center point and the adjacent shank neck and crossing the shank neck. See Schelhas, U.S. Pat. No. 4,822,370. "CCD angle" is a term that is well know in the art and normal or average CCD angles are well documented. See, for example, Schelhas ; Winkler, U.S. Pat. No. 5,376,125; and Vermeire, U.S. Pat. No. 5,004,475. The coupling part 6 comprises a bore 7 into which the peg 4 fits. The diameter of the bore 7 is slightly larger than that of the peg 4, so that the latter can be inserted easily into the bore 7, while still achieving good coupling effect.

At its upper end, the grip part 2 carries an anvil 8. The top side and underside of the anvil 8 form strike surfaces for driving the rasp stem 9 into and extracting the stem 9 from the bone.

Figure 2:
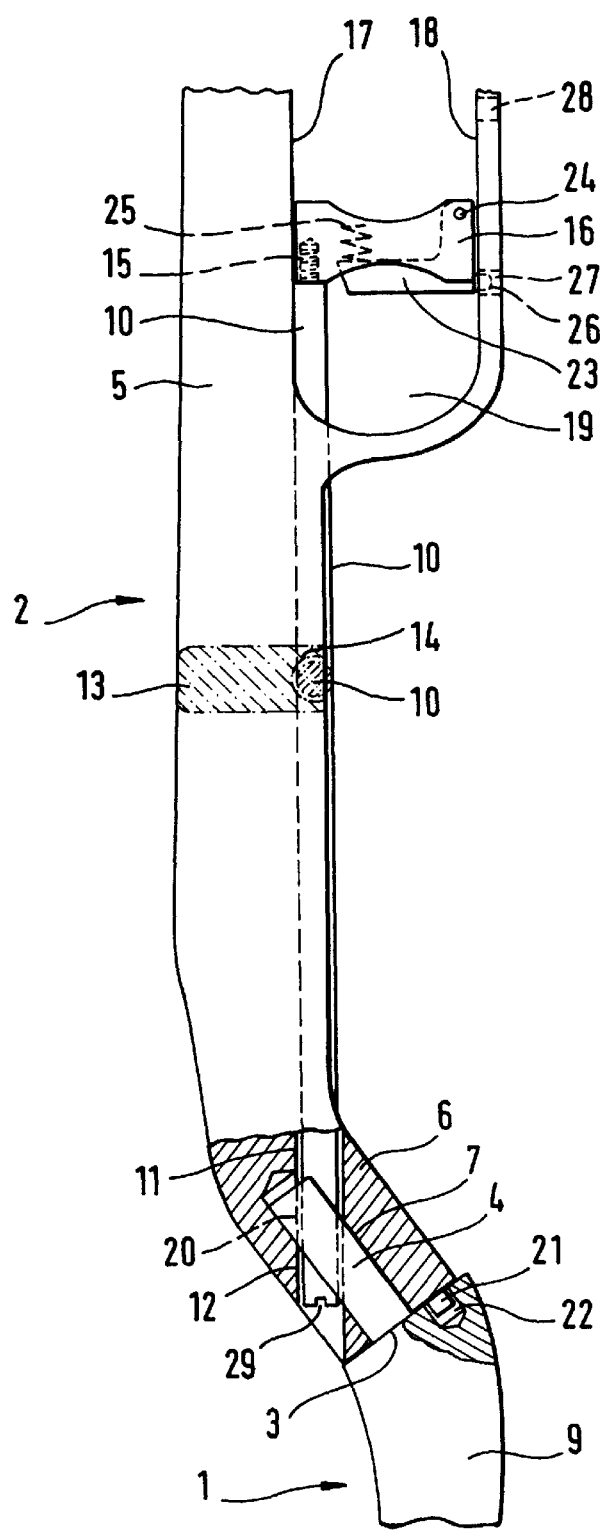
FIG. 2 is an enlarged side view in partial cross-section of the instrument of FIG. 1.

For arresting the peg 4 in the bore 7, use is made of the rod 10 which is guided in the coupling part 6 of the grip part 2 in aligned bores 11, 12 above and below the bore 7. Above the coupling part 6, in the area of the grip stem 5, the rod 10 lies in an outwardly open groove 14 of the grip stem, as indicated at 13 in cross-sectional representation. The upper end of the rod 10 is screwed at 15 into a slide 16 which is guided between the flanks 17, 18 of a grip aperture 19 in the longitudinal direction of the stem 5. The slide 16 forms the handle for longitudinal displacement of the rod 10. The peg 4 of the rasp 1 includes a peg bore 20 which is aligned with the bores 11, 12 in the inserted state. In the position shown in FIG. 2, the lower end of the rod 10 protrudes through this bore 20 and thereby arrests the rod in the bore 7. The rod 10 is able to take up considerable coupling forces since it is guided above and below the peg 4 in the bores 11, 12. The peg 4 is in this way also secured against rotation so that forces can be transmitted not only in the longitudinal direction, but also rotationally from the grip part 2 to the stem 9 of the rasp 1. Nevertheless, it may be expedient to additionally provide an anti-rotation means, which is indicated in FIG. 2 as a projection 21 at the lower end of the coupling part 6 and which engages in a blind bore 22 in the surface 3 of the rasp 1. The projection 21 and the bore 22 are eccentric to the peg 4 and the bore 7, respectively.

When the closed coupling represented in FIG. 2 is to be released, the rod 10 is pulled upwards using the slide 16, until it has left the bore 20 of the peg 4. The grip part 2 can then be easily detached from the rasp 1.

To ensure that the slide 16 cannot inadvertently leave the arrested position or the released position, it is provided with a catch mechanism. The catch mechanism includes a release mechanism 23 mounted about the pivot point 24 on the slide 16. The release mechanism 23 is acted upon by a spring 25 in the anticlockwise direction so that its back (located on the right in the drawing) bears on the flank 18 of the grip aperture 19. There, it has a projection 26 which interacts with a catch opening 27 which designates the arrested position. If appropriate, a further catch opening 28 can be provided, assigned to the released position. If the physician wishes to release the coupling, all he needs to do is to grip with his finger underneath the slide 16, through the grip aperture, and draw his finger upward, the release mechanism 23 being pressed into the slide 16 counter to the spring force until the projection 26 leaves the lock opening 27 and the slide 16 can slide upward together with the rod 10. To close the coupling, the opposite procedure is followed.

The bore 12 is open toward the bottom. The end face of the rod 10 is provided with a screwdriver slot 29 or the like, to permit attachment of a tool with which its screw connection 15 to the slide 16 can be undone. The rod 10 and the slide 16 can then be easily separated from the grip part 2 for cleaning purposes.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A surgical instrument comprising a stem configured to be inserted into a medullary cavity of a proximal femur, and a grip part extending generally parallel to said stem and releasably connected to an upper end of said stem by a coupling comprising a peg protruding obliquely from the upper end of the stem, a bore located in the grip part for receiving the peg, and releasable means for arresting the peg in the bore, wherein the releasable arresting means comprises a rod which is guided movably in the longitudinal direction of the grip part through a guide bore and a recess in the peg for receiving an end of said rod, wherein said recess is a continuous bore and the rod, in an arrested position, is supported on both sides of the peg in the guide bore.

2. The surgical instrument of claim 1, wherein the guide bore is open at its bottom.

3. The surgical instrument of claim 2, wherein the rod is guided openly on a side of the grip part.

4. The surgical instrument of claim 1, wherein an upper end of the rod is connected to a handle which is arranged in a middle to upper region of the grip part.

5. The surgical instrument of claim 1, further comprising a catch mechanism for securing the rod in an arrested position.

6. A surgical instrument comprising a stem having a peg protruding therefrom, said peg having a transverse bore extending therethrough; a grip part connectable to said stem, said grip part having a peg-receiving bore; and releasable locking means for selectively retaining said peg in said peg-receiving bore, said locking means comprising a guide bore that intersects said peg-receiving bore and a rod movably located on said grip part and aligned with said guide bore, wherein said peg is locked in said peg-receiving bore by aligning said transverse bore of said peg with said guide bore and passing an end of said rod through said peg.

7. The surgical instrument of claim 6, further comprising means for securing said rod in said locked position.

8. The surgical instrument of claim 7, wherein said securing means comprises a catch mechanism.

9. The surgical instrument of claim 8, wherein said catch mechanism comprises a release mechanism connected for longitudinal displacement with said rod, and a spring connected to said release mechanism for urging said release mechanism to the locked position.

10. The surgical instrument of claim 9, wherein said grip part further comprises a handle, said handle including a slide guided for movement in the longitudinal direction of the grip part by a pair of spaced flanks, wherein an upper end of said rod is connected to said slide, and wherein said release mechanism is pivotally connected to said slide.

11. The surgical instrument of claim 6, wherein said guide bore has an open bottom.

12. The surgical instrument of claim 6, wherein said grip part further comprises an outwardly opening groove, and wherein said rod lies in said groove.

13. A surgical instrument comprising a stem, a grip part connectable to said stem, releasable locking means for selectively connecting said grip part to said stem, and means for securing said locking means in a locked position, said securing means comprising a catch mechanism, wherein said grip part further comprises a handle, said handle including a slide guided for movement in the longitudinal direction of the grip part, said locking means is connected to said slide, said catch mechanism comprises a release mechanism that is pivotally connected to said slide and a spring for urging said release mechanism toward a flank defining said handle; said flank has a second opening positioned above said first opening, and said spring urges said projection into said second opening when said locking means is in an unlocked position.

14. The instrument of claim 13, wherein said catch mechanism is spring-biased.

15. The instrument of claim 13, wherein said catch mechanism comprises a release mechanism connected to said locking means for longitudinal displacement therewith, and a spring connected to said release mechanism for urging said release mechanism to said locked position.

16. The surgical instrument of claim 9, wherein said grip part further comprises a handle, said handle including a slide guided for movement in the longitudinal direction of the grip part, wherein said locking means is connected to said slide, and wherein said catch mechanism comprises a release mechanism that is pivotally connected to said slide and a spring for urging said release mechanism toward a flank defining said handle.

17. The surgical instrument of claim 16, wherein said release mechanism has a projection extending from an edge thereof, wherein said flank has a first opening defined therein, and wherein said spring urges said projection into said first opening when said locking means is in the locked position.

18. The instrument of claim 13, wherein said stem has a peg protruding therefrom, said peg having a transverse bore extending therethrough; wherein said grip part has a peg-receiving bore; and wherein said releasable locking means comprises a guide bore that intersects said peg-receiving bore and a rod movably located on said grip part and aligned with said guide bore, wherein said peg is locked in said peg-receiving bore by aligning said transverse bore of said peg with said guide bore and passing a lower end of said rod through said transverse bore in said peg.

19. The surgical instrument of claim 8, wherein said catch mechanism is spring-biased.

* * * * *

UNITED STATES PATENT AND TRADEMARK OFFICE
CERTIFICATE OF CORRECTION

PATENT NO. : 6,187,006 B1
DATED : February 13, 2001
INVENTOR(S) : Arnold Keller

It is certified that error appears in the above-identified patent and that said Letters Patent is hereby corrected as shown below:

(30) Foreign Application Priority Data:

Change "298 07 670 U" to -- 298 07 671.3 --

Signed and Sealed this

Twenty-eighth Day of August, 2001

Attest:

Nicholas P. Godici

NICHOLAS P. GODICI
Attesting Officer
Acting Director of the United States Patent and Trademark Office